United States Patent
Maxwell, III

(10) Patent No.: US 7,507,583 B2
(45) Date of Patent: Mar. 24, 2009

(54) ANALYSIS OF LARGE SOIL SAMPLES FOR ACTINIDES

(75) Inventor: Sherrod L. Maxwell, III, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 583 days.

(21) Appl. No.: 11/390,229

(22) Filed: Mar. 27, 2006

(65) Prior Publication Data

US 2007/0224687 A1 Sep. 27, 2007

(51) Int. Cl.
*G01N 33/42* (2006.01)
*G01N 33/24* (2006.01)

(52) U.S. Cl. .............. 436/82; 436/73; 436/74

(58) Field of Classification Search .......... 436/73, 436/74, 82
See application file for complete search history.

(56) References Cited

U.S. PATENT DOCUMENTS

| 4,724,217 | A | * | 2/1988 | Miller | 436/82 |
|---|---|---|---|---|---|
| 4,835,107 | A | * | 5/1989 | Horwitz et al. | 436/82 |
| 5,190,881 | A | * | 3/1993 | McKibbin | 436/82 |
| 5,205,999 | A | * | 4/1993 | Willis et al. | 423/20 |
| 5,651,883 | A | * | 7/1997 | Horwitz et al. | 210/198.2 |
| 5,928,517 | A | * | 7/1999 | Smith et al. | 210/650 |
| 5,945,342 | A | | 8/1999 | Maxwell, III et al. | |
| 6,635,796 | B2 | | 10/2003 | Pal et al. | |
| 6,881,541 | B2 | * | 4/2005 | Petersen et al. | 435/6 |
| 7,368,412 | B2 | * | 5/2008 | Tranter et al. | 502/406 |

* cited by examiner

*Primary Examiner*—Jill Warden
*Assistant Examiner*—Rebecca Fritchman
(74) *Attorney, Agent, or Firm*—McNair Law Firm, P.A.; William D. Lee, Jr.

(57) ABSTRACT

A method of analyzing relatively large soil samples for actinides by employing a separation process that includes cerium fluoride precipitation for removing the soil matrix and precipitates plutonium, americium, and curium with cerium and hydrofluoric acid followed by separating these actinides using chromatography cartridges.

4 Claims, No Drawings

ANALYSIS OF LARGE SOIL SAMPLES FOR ACTINIDES

The United States Government has rights in this invention pursuant to Contract No. DE-AC09-96SR18500 between the U.S. Department of Energy and Washington Savannah River Company, LLC.

FIELD OF THE INVENTION

This invention relates to a method for separating and analyzing actinides in relatively large soil samples, a large soil sample being in the range of 100 to 200 grams or greater.

BACKGROUND OF THE INVENTION

The group of elements known as the actinides is the elements from actinium, atomic number 89, to lawrencium, atomic number 103. All the elements in this series can resemble actinium in their chemical and electronic properties so that they form a separate group of elements within the periodic table.

All actinides are metals and all are radioactive. They emit energy in the form of alpha particles, beta particles, or gamma rays and by emitting these particles or photons, the actinide atom loses protons and as a result becomes another element with a lower atomic number. The actinides undergo radioactive decay at different rates, that is, they have different half-lives. The elements with the higher atomic numbers generally have short half-lives and rapid radioactive decay. Some actinides with lower atomic numbers have half-lives that can be thousands or even millions of years.

The two actinides of most general interest are uranium and plutonium, uranium being a naturally occurring element whereas plutonium is a created element.

Environmental contamination by actinides is a major concern around facilities that engage in activities that use or produce actinides or facilities where nuclear stockpiles are maintained. The actinides such as uranium, neptunium, plutonium, and americium are major contributors to the long-term activity of nuclear waste which must be stored at remote sites. In order to determine the long-term safety of storage sites, testing of soil samples is of prime interest in evaluating the safety of such storage sites.

Of the actinides and their isotopes, plutonium is perhaps the most complex element in the periodic table because it may assume one of six different forms or phases, each with a different density and volume. Because of plutonium's behavior, it receives special concern for not only its handling but for its detection. A very large sample size is not needed to adequately measure uranium in soil due to its relatively high level compared to other actinides such as plutonium and americium; and, because of the difficulty of detecting plutonium; a larger soil sample is required.

However, in a large soil sample the amount of uranium that is present interferes with plutonium and americium detection methods. As a result, steps must be taken to prevent uranium interference in plutonium and americium chemical recoveries.

Accordingly, it is an object of the present invention to provide a method for detecting plutonium, americium, and curium isotopes in relatively large soil samples.

In U.S. Pat. No. 5,190,881 to Terry T. McKibbon a process is described for analyzing human waste for actinides. Uranium accompanies the plutonium through the extraction process but is separated from the plutonium in the cerium fluoride precipitation step, the uranium staying in the filtrate. The uranium can be recovered by the addition of titanous chloride and more cerium carrier to the fluoride filtrate. The fractions are electrodeposited or carried by cerium fluoride on filter paper and analyzed by alpha spectrometry for isotope identification and quantification.

Accordingly, it is another object of the present invention to provide an effective and simple method for analyzing samples for actinides by employing cerium fluoride precipitation.

The above and additional objects are achieved by this invention which is described below.

SUMMARY OF THE INVENTION

The novel method of the invention allows the measurements of actinides to very low detection levels. This is important not only in the United States but is, perhaps, more important in Europe to meet regulatory standards. The method employs a novel cerium fluoride precipitation matrix removal step to precipitate plutonium, americium, and curium and separate these actinides on small extraction chromatography cartridges. Heretofore there were no analytical methods that were able to accomplish this easily and effectively.

Accordingly, in one aspect, the present invention is a method of using cerium fluoride precipitation to remove the difficult soil matrix in samples of soil in the range of 100 to 200 grams or greater whereby the actinides can be separated and analyzed by small stacked extraction chromatography cartridges. These cartridges can not be used with large samples without the soil matrix removal method.

DETAILED DESCRIPTION

The need to measure actinides at extremely low levels is very important to meet regulatory requirements. However, the measurement of actinides in very large soil samples of 100 to 200 grams in size is quite difficult. The present invention provides a novel method to analyze very large samples for actinides such as plutonium, americium and curium isotopes and employs curium fluoride precipitation to remove the difficult matrix so that the actinides can be separated and analyzed using small stacked extraction chromatographic extraction cartridges which are available from Eichrom Technologies of Darien, ILL. As mentioned above, these cartridges can not be used with large samples unless the soil matrix removal of the present invention is used.

In a preferred embodiment and best mode of the present invention, soil is leached with nitric and hydrochloric acids centrifuged and filtered to collect the leachate containing plutonium, americium, and curium. This leachate is fused using 20 grams of sodium hydroxide at 600° C. in a zirconium crucible. An iron hydroxide precipitation process is then performed. Cerium is added to facilitate chemical recoveries and titanium chloride reductant is added to complex the carbonate. After acid dissolution, cerium fluoride precipitation is used to further separate actinides from the soil matrix. Hydrogen peroxide is added to oxidize any uranium present and prevent uranium precipitation. Additional cerium is added, followed by hydrofluoric acid to precipitate the actinides with cerium. After redissolution of the cerium fluoride precipitate, stacked cartridges are used to separate the plutonium, americium, and curium for assay by alpha spectrometry which is well-known to those skilled in the art. The stacked cartridges employ TEVA Resin+TRU Resin+DGA Resin to separate plutonium, americium and curium by using alpha spectrometry.

Detailed information regarding the stacked cartridge process for arraying actinide may be found in an article entitled "Rapid Column Extractor Method for 5 Urine" by Sherrod L. Maxwell, et al., Westinghouse Savannah River Co., Document No. WSR-MS-2000-00372 which article is incorporated herein by reference.

The foregoing soil matrix removal process is quick and effective so that it uniquely allows the use of small two ml resin cartridges for separation of actinides from 200 gram soil samples. Prior methods get inconsistent chemical recoveries and must be used with very large ion exchange columns that generate large quantities of liquid waste. The prior methods do not generally include a fusion step and are less rugged regarding dissolution of refractory actinide particles. The present method provides effective removal of interferences and high chemical yields.

While a preferred embodiment of the invention has been disclosed, various modes of carrying out the principles disclosed herein are contemplated as being within the scope of the following claims. Therefore, it is understood that the scope of the invention is not to be limited except as otherwise set forth in the claims.

What is claimed is:

1. A method of analyzing soil samples for the presence of actinides comprising the steps of:
   a) collecting a soil sample;
   b) leaching said soil with an acid;
   c) collecting the leachate;
   d) fusing the collected leachate with a base at an elevated temperature;
   e) precipitating the fused leachate with iron hydroxide and adding cerium to enhance actinide precipitation;
   f) adding complexing agents to complex the carbonate followed by acid dissolution;
   g) re-precipitating with cerium fluoride to further separate the actinides from the soil matrix;
   h) oxidizing any uranium present to prevent uranium precipitation;
   i) adding cerium and hydrofluoric acid to precipitate the actinides;
   j) redissolving the cerium fluoride precipitate;
   k) separating the plutonium, americium, and curium using stacked cartridges; and
   l) assaying the plutonium, americium, and curium by alpha spectrometry.

2. A method of analyzing soil samples for the presence of actinides comprising the steps of:
   a) collecting a soil in a sample of at least about 100 grams;
   b) leaching said soil with nitric and hydrochloric acids;
   c) centrifuging and filtering to collect the leachate, said leachate containing plutonium, americium, and curium;
   d) fusing the collected leachate with sodium hydroxide at an elevated temperature;
   e) precipitating the fused leachate with iron hydroxide and adding cerium for facilitating chemical recoveries;
   f) adding titanium chloride reductant and barium to complex the carbonate followed by acid dissolution;
   g) further separating the actinides from the soil matrix by precipitating the recovered reactants from the foregoing step with cerium fluoride;
   h) adding hydrogen peroxide to oxidize any uranium present and prevent uranium precipitation;
   i) adding cerium and hydrofluoric acid to precipitate the actinides with cerium;
   j) redissolving the cerium fluoride precipitate;
   k) separating the plutonium, americium, and curium using the stacked cartridge process; and
   l) assaying said actinides by alpha spectrometry.

3. The method of claim 2 wherein the weight of the collected sample of soil is in the range from about 100 grams to about 200 grams.

4. The method of claim 3 wherein in step d about 20 grams of sodium hydroxide is added to the leachate in a zirconium crucible at a temperature of about 600° C.

* * * * *